United States Patent [19]

Ozbey et al.

[11] 4,106,501
[45] Aug. 15, 1978

[54] SWEEPING FLUID SPRAY ORAL HYGIENE DEVICE

[76] Inventors: Amber Lola Ozbey; Ahmet M. Ozbey, both of 8221 Clay Dr., Oxon Hill, Md. 20022

[21] Appl. No.: 776,759
[22] Filed: Mar. 11, 1977
[51] Int. Cl.² .............................................. A61C 15/00
[52] U.S. Cl. .................................. 128/62 A; 32/40 R
[58] Field of Search ............. 128/62 A, 239; 32/40 R

[56] References Cited

U.S. PATENT DOCUMENTS

| 3,379,192 | 4/1968 | Warren, Jr. | 128/62 A |
| 3,527,218 | 9/1970 | Westline | 128/62 A |
| 3,874,084 | 4/1975 | Cole | 128/62 A |

Primary Examiner—Robert Peshock
Attorney, Agent, or Firm—Sixbey, Friedman and Leedom

[57] ABSTRACT

The fluid spray oral hygiene device includes a resilient mouthpiece with upper and lower channels to receive the teeth of a user. Fluid jet forming nozzles in the walls of each channel direct fluid jets against the teeth, and as the user chews on the mouthpiece, these jets pulsate and sweep up and down across the teeth and gums. A valve response to pressure from the teeth is included in the mouthpiece to control the flow of fluid thereto.

16 Claims, 4 Drawing Figures

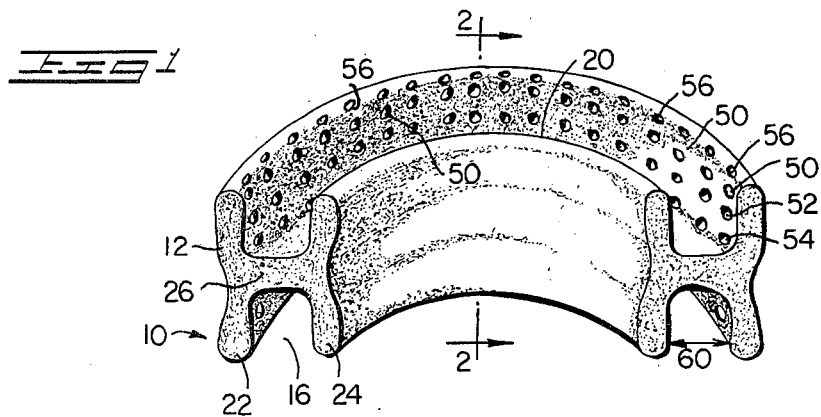
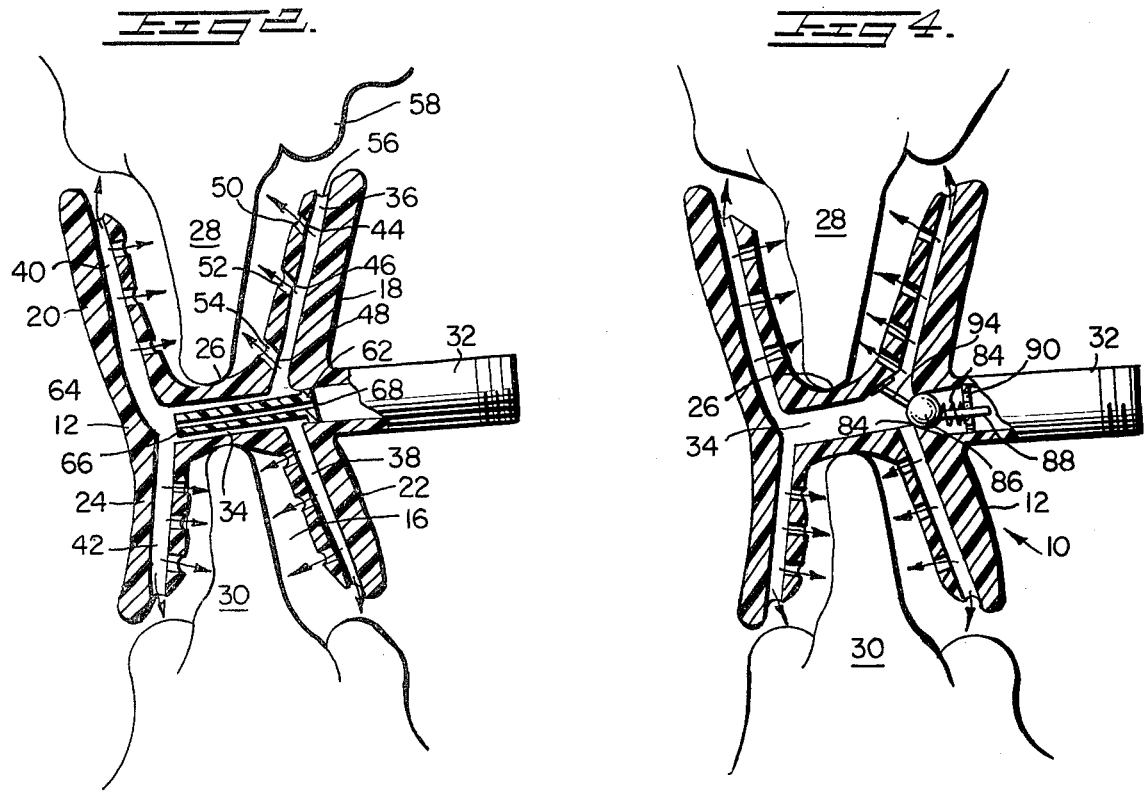
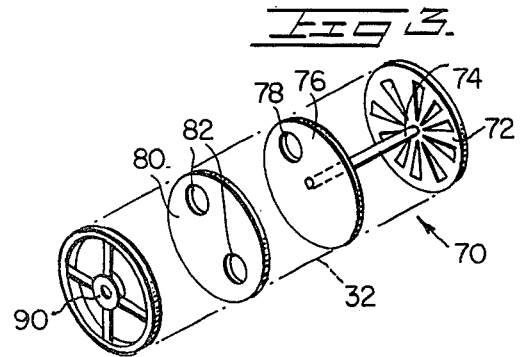

SWEEPING FLUID SPRAY ORAL HYGIENE DEVICE

BACKGROUND OF THE INVENTION

This invention relates to a device for use in the daily care of human teeth and gums. More particularly, this invention relates to a mouthpiece type device for cleaning the teeth and gums with a plurality of fluid spray jets operated in a new and novel way.

In the prior art, a number of methods and devices have been developed for caring for the teeth and gums. The toothbrush, one of the oldest implements in the art, has recently been recognized as an inept solution to the problem of oral hygiene care. Not only has the usage of the toothbrush generally been inadequate in terms of the amount of time and energy devoted to each brushing, but even when properly used, the toothbrush cannot reach many of the harmful organisms found in the crevices of the teeth and gums. With continued usage, the nylon bristles found in many toothbrushes cause significant damage to both the tooth surfaces and the supporting gum tissue.

Mouthpiece type toothbrushes have been developed to simultaneously clean a plurality of tooth and gum surfaces as shown by U.S. Pat. No. 3,874,084 to W. Cole. Although these devices do contact a larger surface than the conventional toothbrush, they are still subject to the same deficiencies as the toothbrush.

One attempt to answer the problems presented by toothbrush type structures has appeared in the form of a fluid jet or spray device. The fluid jet device represents an improvement over the toothbrush inasmuch as it is able to more effectively remove bacterial deposits and food residue from between the teeth and gums.

Initially, fluid jet devices appeared in the form of a modified toothbrush which merely issued fluid jets from the head of the brush. Unfortunately, although these new devices cleaned the teeth and gums better than ordinary toothbrushes, they only did a better cleaning job on the areas where the fluid jets were manually directed, and hence were susceptible to the same improper usage which contributed to the inadequacy of the toothbrush.

To avoid this problem, cuff like members which embraced the teeth and gums were developed which included internal chambers to receive fluid. A plurality of perforations were provided in these inner chambers from which fluid under pressure could be emitted in the form of jet streams against the teeth and gums. Such devices are disclosed in a plurality of issued United States patents as exemplified by U.S. Pat. Nos. 3,379,192, 3,481,329 and 3,489,141 to L. G. Warren, Jr., 3,527,218 to J. R. Westline and 3,669,101 to W. Kleiner. In each of these devices, the user merely places the cuff-like member in his mouth and applies fluid under pressure to the member, usually from a nearby water faucet. The teeth and gums are then simultaneously and automatically cleaned by a plurality of fluid jets.

In actuality, however, these mouthpiece type fluid jet devices have not proven to be the ideal solution to inadequate oral hygiene. Even with the use of a plurality of stationary fluid jets directed against the tooth and gum surfaces, some areas still do not receive direct bombardment by the jet spray and hence are not adequately cleaned. It is impossible to have jet sprays directed toward every area of the tooth and gums since this would require essentially an infinite number of jet sprays.

In the event a structure could be made which could eject a nearly infinite number of jet sprays, the available fluid supply would not provide enough pressure to accomplish adequate cleaning. Also close proximity of the jets would cause the fluid first arriving at the surface of the teeth and gums to form a fluid film over the food residue to be removed. This fluid film then would act to buffer the food residue from the direct impact of subsequent fluid; a phenomena described in U.S. Pat. No. 3,870,039 to Moret et al.

Of even greater importance is the fact that a mouthpiece fluid jet device designed to provide a large number of jet sprays would multiply the greatest problem experienced with mouthpiece plural jet devices; namely the fluid drainage problem. With all known mouthpiece devices, water flows continuously from a plurality of orifices until a faucet or other remote valve is manually operated. Water soon fills the oral cavities of a user and it is then difficult for the user to eject water through the mouth faster than water is provided to the mouthpiece. Should a user choke while the mouthpiece is receiving water, it is often impossible to manually manipulate a remote valve rapidly enough to prevent serious choking on the incoming water. The only effective remedy with present devices is to remove the mouthpiece which is still spraying water with the result that everything within range is thoroughly soaked.

Accordingly, it is an object of this invention to provide a fluid spray device for oral hygiene which obviates the problems of the prior art devices.

A more specific object of this invention is to provide a novel and improved fluid spray device for bombarding the teeth and gums with a plurality of non-stationary fluid jet sprays which sweep across the teeth and gum surfaces in response to a chewing motion by the user.

Another object of this invention is to provide a novel and improved fluid spray device adapted to direct fluid jet sprays against the teeth and gums of a user which includes a valve actuated by the teeth of a user to control the flow of fluid to the device; and A still further object of the present invention is to provide a novel and improved fluid spray device adapted to direct pulsating fluid jet sprays against the teeth and gums in a sweeping up and down movement in response to chewing motions by a user.

BRIEF DESCRIPTION OF THE INVENTION

The present invention utilizes a special resilient mouthpiece which, when properly placed in the mouth of the user, surrounds and separates both the upper and lower teeth.

Fluid under pressure is provided through a flexible fluid carrying conduit to the front portion of this mouthpiece and exits in the form of high speed fluid jets from a plurality of small perforations located on the inner portions of the mouthpiece adjacent the teeth and gums of the user.

The mouthpiece is designed so that when the user bites down on the mouthpiece, vertical walls adjacent the teeth move inwardly causing the fluid jets coming from perforations on these walls to sweep downwardly. Hence as the user chews on the mouthpiece, a plurality of pulsating fluid jet streams sweep vertically back and forth from the exposed tip of the teeth during maximum mouthpiece compression to the gingival crevices during minimum mouthpiece compression. The result is a fluid spray oral hygiene device which sprays jet fluid streams directly on most of the tooth and gum surfaces without the above mentioned problems of low pressure, fluid film buildup, or excessive flooding of the mouth present with static fluid jet spray devices. Also the present device includes a flow valve actuated by the user's teeth so that fluid flow into the device may be stopped or started instantly without removing the mouthpiece of the device from the mouth of the user.

DESCRIPTION OF THE DRAWINGS

FIG. 1 is a perspective view of the mouthpiece for the fluid spray oral hygiene device of the present invention;

FIG. 2 is a sectional view of the fluid spray oral hygiene device of the present invention taken along lines 2—2 of FIG. 1;

FIG. 3 is an exploded view of a fluid pulsator for the fluid spray oral hygiene device of the present invention; and FIG. 4 is a sectional view of a second embodiment of the fluid spray oral hygiene device of the present invention taken along lines 2—2 of FIG. 1.

Referring now to FIGS. 1 and 2, the fluid spray oral hygiene device of the present invention indicated generally at 10 includes a mouthpiece 12 having an upper channel 14 which is constructed to conform generally to an upper dental arch and a lower channel 16 which is constructed to conform generally to a lower dental arch. Upper channel 14 is defined by a vertically extending front wall 18 which is spaced from a vertically extending rear wall 20. Similarly, the bottom channel 16 is defined by a vertically extending front wall 22 which is spaced from a vertically extending rear wall 24. The bottom wall of the upper and lower channels 14 and 16 is formed by a central web 26 which extends horizontally between the front and rear walls of the upper and lower channels.

As will be noted from FIG. 2, when the upper teeth 28 and lower teeth 30 of a user are inserted into the upper and lower channels of the mouthpiece 12, the inner surfaces of the vertically extending walls 18, 20, 22 and 24 are spaced from the upper and lower teeth. Thus, the walls of the channels 14 and 16 do not tightly engage the teeth, but instead, space is provided for these walls to move toward the teeth in a manner to be subsequently described.

Fluid is furnished to the mouthpiece 12 through an inlet port 32 secured to the front surface of the mouthpiece. This inlet port is adapted for connection in any known manner to a flexible hose or conduit which may be in turn connected to a conventional faucet. Thus water under pressure will be provided from the faucet through the conduit to the inlet port 32 and the mouthpiece 12. The inlet port communicates with a horizontally extending chamber 34 formed centrally through the web 26. Communicating with this chamber 34 are vertically extending branch chambers or conduits 36, 38, 40, and 42 which are provided internally within the front walls 18 and 22 and the rear walls 20 and 24 respectively.

The vertically extending branch chambers or conduits 36, 38, 40 and 42 provide fluid to a plurality of outlet nozzles which direct fluid onto the upper and lower teeth 28 and 30. A plurality of these outlet nozzles extend from each branch chamber or conduit and terminate in a small opening or aperture formed at the inner surface of one of the vertical walls of the mouthpiece. Since all of these nozzles are substantially identical in structure, the nozzles operating in conjunction with vertical conduit 36 will be considered in detail. It will be noted that vertical conduit 36 communicates with a plurality of short nozzles 44, 46 and 48 which terminate respectively in apertures 50, 52 and 54. These nozzles are angled slightly upwardly so that fluid therefrom is ejected toward the upper teeth 28 at a slightly upward angle when the mouthpiece 12 is in an uncompressed condition. The arrows in FIG. 2 indicate the normal direction of each fluid stream with the mouthpiece in this condition.

In addition to the nozzles 44, 46, and 48, the vertical chamber 36 also communicates with an aperture 56 formed on the upper edge of the wall 18. This aperture 56 directs fluid upwardly toward the gum 58 for the upper teeth 28.

As previously indicated, the front wall 22 and the rear walls 20 and 24 all include nozzles 44 and apertures 50, 52, 54 and 56 corresponding to those described in connection with the front wall 18. As will be apparent from the arrows in FIG. 2, these nozzles are formed so that when the mouthpiece 12 is in an uncompressed condition, the fluid jet streams issuing from the nozzles are directed angularly away from the web 26 which constitutes the bottom of the upper and lower channels 14 and 16. Also, it will be noted that the width of the upper and lower channels indicated at 60 in FIG. 1 is sufficient to ensure that the walls 18, 20, 22 and 24 are spaced from the teeth 28 and 30 so that movement of these walls is facilitated.

The mouthpiece 12 is moulded from resilient material such as rubber or flexible plastics so that flexure occurs in response to a chewing motion by the teeth 28 and 30. As the teeth 28 and 30 come together against the web 26, the web is compressed into the chamber 34 causing the free ends of the walls 18 and 20 and the walls 22 and 24 to move inwardly toward the teeth 28 and 30. Actually, the free ends of these walls tend to pivot about the point where the walls connect to the web 26. At the same time, compression of the web tends to move the inner surfaces of the channel defining walls downwardly toward the web. Thus it will be seen that compression of the web angles the fluid jets emitted from the apertures 50, 52, 54 and 56 downwardly in the channels 14 and 16 as the channel walls flex inwardly and move downwardly. Then, as pressure on the web 26 is released, the channel walls move upwardly and outwardly causing the fluid jets to again angle upwardly from the channels. As the chewing motion on the web continues, the channel walls move back and forth and up and down causing the fluid jets emitted therefrom to sweep up and down the teeth 28 and 30 and the adjoining gum surfaces. This movement of the fluid jets up and down along the teeth and gums parallels the ideal brushing movement for a toothbrush, and effectively removes foreign matter from the teeth and gums. Additionally, since the fluid jets are normally angled upwardly from the channels 14 and 16, fluid carrying foreign matter is ejected from the channels each time pressure is released on the web 26.

Ideally, the jets of fluid issuing from the apertures 50, 52, 54 and 56 should be pulsating jets of fluid, and this pulsating occurs as a result of the structure of the mouthpiece 12. Initially, with the web 26 in an uncompressed position, fluid from the inlet port 32 fills the chamber 34 and the branch conduits 36, 38, 40 and 42. As the teeth 28 and 30 compress the web 26 and the chamber 34, a pumping action occurs which forces a pulse of fluid out through the apertures 50, 52, 54 and 56. When the pressure of the teeth on the web is released during a chewing motion, fluid again fills the internal chambers of the mouthpiece 12, so that a second pressure pulse will occur when the teeth again move together against the web.

It is desirable that the mouthpiece 12 be provided with valve means to control the flow of fluid into the chamber 34 from the inlet port 32. For this purpose, a flapper valve 62 is provided across the inner end of the inlet port 32. This flapper valve has spaced resilient upper and lower walls 64 and 66 respectively which are joined by flexible sidewalls 68, one of which is shown in FIG. 2. Normally, fluid from the inlet port 32 passes between the upper and lower walls 64 and 66 of the flapper valve and is emitted from the open end of the flapper valve into the chamber 34. However, if a user of the mouthpiece desires to substantially terminate fluid flow into the mouthpiece, the user, by biting down hard on the web 26, can cause the walls of the web to contact and bring together the upper and lower walls of the flapper valve. Thus the flapper valve can be held closed as long as the teeth of the user are clamped down hard on the web 26, and this will provide time for the user to eject excess fluid from the oral cavities before again permitting fluid to flow into the mouthpiece 12. In an emergency situation where the user chokes, fluid flow can be immediately terminated by clamping the teeth 28 and 30 together against the web 26, thus providing time for the user to manually manipulate a faucet to permanently shut-off the fluid supply to the mouthpiece. However, no fluid is being provided to the mouthpiece to further choke the user while this manual manipulation occurs.

As will be noted from FIG. 1, the apertures 50, 52, 54 and 56 are provided in a plurality of vertical rows across the extent of the mouthpiece 12. Any number of apertures or any arrangement thereof may be employed in the mouthpiece design. Also, a separate branch channel or conduit 48 may be provided for each vertical row of apertures in one of the walls of the mouthpiece, or, the branch channel may constitute a single chamber extending across the extent of the mouthpiece and serving all of the vertical rows of apertures in any single wall.

In some instances, it has been found desirable to enhance the pulsating effect of the fluid jets accomplished by chewing on the web 26 by including a mechanical fluid pulsating device in the inlet port 32. Any known fluid pulsating unit can be employed, but the unit indicated generally at 70 in FIG. 3 is exemplary of a simple unit designed for use with a mouthpiece 12. Referring to FIG. 3, water flowing from a water source into the inlet port 32 contacts a simple turbine wheel 72 and causes this wheel to rotate. The turbine wheel 72 is connected by means of a shaft 74 to a disc unit 76 which substantially closes off the inlet port 32 and permits fluid to flow only through an opening 78. The shaft 74 causes the disc 76 to rotate with the turbine wheel 72, and the disc 76 is engaged against a stationary disc 80 which also closes off the inlet port. Stationary disc 80 is provided with one or more openings 82 through which fluid can flow, and these openings are positioned to align with the opening 78 periodically as the disc 76 rotates. Thus, when the opening 78 is aligned with one of the openings 82, fluid is permitted to flow through the inlet port 32 into the mouthpiece 12, while fluid flow is terminated during the periods that the opening 78 is not aligned with one of the openings 82. Thus a pulsating fluid supply is provided to the mouthpiece 12.

In some embodiments, it is desirable to provide a fluid control valve in the mouthpiece 12 which operates to terminate flow of fluid to the mouthpiece when pressure is removed from the web 26. Such a valve is illustrated in FIG. 4 wherein a valve seat 84 is formed at the point where fluid from the inlet port 32 enters the chamber 34. This valve seat is adapted to receive a ball valve 86 which, when seated upon the valve seat 84, prevents fluid from entering the chamber 34. The ball valve 86 is provided with a guide rod 88 which extends through a hub 90 mounted in the end of the inlet port 32. The hub 90 permits the guide rod to slide longitudinally of the inlet port 32 so that the ball valve 86 is permitted to move toward and away from the valve seat 84. In some instances, it may be desirable to spring bias the ball valve toward the valve seat by means of a spring 92 positioned about the shaft 88 and extending between the hub 90 and the ball valve.

The ball valve 86 is provided with a cam type valve actuator 94 which extends into the chamber 34 to a point closely adjacent the inner surface of the web 26. Thus, when the web 26 is slightly compressed by the teeth 28 and 30 of a person using the mouthpiece 12, the wall of the web contacts the cam actuator 94 and causes the ball valve 86 to move away from the valve seat 84 against the bias of the spring 92. Fluid is not permitted to flow freely into the chamber 34 as long as the web 26 is compressed by the teeth of the user. However, if the teeth 28 and 30 are withdrawn from contact with the web 26, the ball valve 86 is biased into contact with the valve seat 84, and all fluid to the mouthpiece 12 is shut off. Thus, the mouthpiece may be safely removed from the mouth of the user without the necessity to manually manipulate a remote faucet or control valve for the fluid supply.

We claim

1. A fluid jet spray oral hygiene device for cleaning the teeth and gums comprising a mouthpiece having at least one channel to receive the teeth of a user, said channel being defined by a front wall, a rear wall spaced from said front wall and web means extending between said front and rear walls at one end thereof, conduit means for supplying fluid to said mouthpiece, fluid jet forming means provided in said front and rear walls for directing a plurality of fluid jets into said channel against the teeth of a user, and fluid conducting means formed in said mouthpiece for connecting said fluid jet forming means to said conduit means, said web means operating in response to the application and release of pressure when a user chews upon the web means to move the free ends of said front and rear walls toward and away from the teeth to cause said fluid jets to sweep up and down the surface of the teeth of a user.

2. The fluid jet spray oral hygiene device of claim 1, which includes valve means for controlling the flow of fluid to said mouthpiece from said conduit means, said valve means operating in response to pressure applied by the teeth of a user to said web means.

3. The fluid jet spray oral hygiene device of claim 1 wherein said fluid conducting means includes a fluid chamber connected to said conduit means and formed internally in said web means between said front and rear walls, said web means operating in response to downward pressure from the teeth of a user to force fluid from said fluid chamber to said fluid jet forming means to increase the pressure of the fluid jets directed into said channel.

4. The fluid jet spray oral hygiene device of claim 1 wherein said web means causes said fluid jets to pulsate in response to chewing by the user on said web means.

5. The fluid jet spray oral hygiene device of claim 1 wherein said conduit means includes fluid pulsating means to cause said fluid jets to pulsate.

6. The fluid jet spray oral hygiene device of claim 1 wherein said fluid jet forming means are positioned to direct said fluid jets at an upward angle into said channel away from said web means when pressure is not applied to said web means by the teeth of a user.

7. The fluid jet spray oral hygiene device of claim 1 wherein said mouthpiece includes an upwardly opening upper channel and a downwardly opening lower channel, said web means extending between the front and rear walls of said upper and lower channels.

8. The fluid jet spray oral hygiene device of claim 2 wherein said web means is formed of resilient material, said valve means operating in response to substantial indentation of said web means by the teeth of a user to substantially terminate the flow of fluid to said mouthpiece.

9. The fluid jet spray oral hygiene device of claim 2 wherein said valve means operates in response to the application of pressure to said web means by the teeth of a user to cause fluid to flow to the mouthpiece and to terminate said fluid flow upon the removal of the pressure on said web means.

10. The fluid jet spray oral hygiene device of claim 1 wherein said web means is formed of resilient material and includes an internal fluid chamber connected to said conduit means and extending between said front and rear walls, said web means being indented in response to pressure from the teeth of a user to compress said internal fluid chamber and cause movement of said front and rear walls.

11. The fluid jet spray oral hygiene device of claim 10 wherein said internal fluid chamber is compressed and expanded by the chewing action of the teeth of a user on said web means to cause said fluid jets to pulsate.

12. The fluid jet spray oral hygiene device of claim 11 which includes valve means for controlling the flow of fluid to said mouthpiece from said conduit means, said valve means operating in response to pressure applied by the teeth of a user to said web means.

13. The fluid jet spray oral hygiene device of claim 11 wherein said mouthpiece includes an upwardly opening upper channel to receive the upper teeth of a user and a downwardly opening lower channel to receive the lower teeth of a user, said web means extending between the front and rear walls of said upper and lower channels and operating to cause said front and rear walls to simultaneously move up and down and toward and away from the teeth of a user as the internal fluid chamber in said web means is compressed and expanded by the chewing action of the teeth of the user on said web means.

14. The fluid jet spray oral hygiene device of claim 13 which includes valve means mounted between said conduit means and said internal fluid chamber for controlling the flow of fluid from said conduit means, said valve means operating in response to the application of pressure to said web means by the teeth of a user to cause fluid to flow from said conduit means to said internal fluid chamber and to terminate said fluid flow upon the removal of the pressure on said web means.

15. The fluid jet spray oral hygiene device of claim 13 which includes valve means mounted between said conduit means and said internal fluid chamber for controlling the flow of fluid from said conduit means, said valve means operating in response to substantial indentation of said web means by the upper and lower teeth of a user to substantially terminate the flow of fluid from said conduit means to said internal fluid chamber.

16. The fluid jet spray oral hygiene device of claim 13 wherein said fluid jet forming means are positioned to direct said fluid jets angularly into said upper and lower channels at an angle away from said web means when pressure is not applied to said web means by the teeth of a user.

* * * * *